United States Patent
Hoshi (12)

(10) Patent No.: US 6,211,118 B1
(45) Date of Patent: Apr. 3, 2001

(54) HERBICIDAL COMPOSITIONS

(75) Inventor: Hisayuki Hoshi, Toyonaka (JP)

(73) Assignee: Sumitomo Chemical Company, Limited, Osaka (JP)

( * ) Notice: Subject to any disclaimer, the term of this patent is extended or adjusted under 35 U.S.C. 154(b) by 0 days.

(21) Appl. No.: 09/372,982

(22) Filed: Aug. 12, 1999

(30) Foreign Application Priority Data

Aug. 12, 1998 (JP) .................................. 10-227986

(51) Int. Cl.[7] ........................................ A01N 43/64
(52) U.S. Cl. .................................... 504/134; 504/136
(58) Field of Search ..................... 504/134, 136

(56) References Cited

U.S. PATENT DOCUMENTS 5,534,482 * 7/1996 Ishida et al. ................... 504/215

FOREIGN PATENT DOCUMENTS

19834627 * 7/1998 (DE) .
9707104   2/1997 (WO) .
9836642 * 8/1998 (WO) .
9854967 * 12/1998 (WO) .

* cited by examiner

Primary Examiner—Jose G. Dees
Assistant Examiner—Alton Pryor
(74) Attorney, Agent, or Firm—Birch, Stewart, Kolasch & Birch, LLP

(57) ABSTRACT

Provided are herbicidal compositions comprising 2-chloro-4-fluoro-5-(4-methyl-5-trifluoromethyl-3-pyridazinon-2-yl) phenyl C1-C5 non-cyclic hydrocarbyl ether in combination with a second herbicidal compound selected from a group consisting of 1-(2-ethylsulfonylimidazo[1,2-a]pyridin-3-ylsulfonyl)-3-(4,6-dimethoxypyrimidin-2-yl) urea, 2-(2-trifluoromethoxy-phenyl-sulfonylaminocarbonyl)-4-methyl-5-methoxy-2,4-dihydro-3H-1,2,4-triazol-3-one, methyl 4-iodo-2-[[[[(4-methoxy-6-methyl-1,3,5-triazin-2-yl)amino]carbonyl]amino]sulfonyl]benzoate, and methyl 2-[4,6-dimethoxypyrimidin-2-ylcarbamoyl)sulfamoyl]-6-(trifluoromethyl)nicotinate, monosodium salt. Methods of controlling a weed or weeds are also provided in the instant invention.

14 Claims, No Drawings

HERBICIDAL COMPOSITIONS

FIELD OF THE INVENTION

The instant invention relates to herbicidal compositions and methods of controlling a weed.

BACKGROUND OF THE INVENTION

At present, there are many types of weeds that can be controlled by utilizing herbicidal compositions. There also are weeds that additionally occupy an extended growing season. For these reasons, numerous herbicides are commercially available and are widely used to control such weeds. However, herbicidal compositions that do not cause phytotoxicity to crops and which posses a high herbicidal activity and broad herbicidal spectrum are desirous.

2-chloro-4-fluoro-5-(4-methyl-5-trifluoromethyl-3-pyridazinon-2-yl)phenyl $C_{1-5}$ non-cyclic hydrocarbyl ether compounds are known to posses a herbicidal activity. In addition, 1-(2-ethylsulfonylimidazo[1,2-a]pyridin-3-ylsulfonyl)-3-(4,6-dimethoxypyrimidin-2-yl) urea, 2-(2-trifluoromethoxy-phenyl-sulfonylaminocarbonyl)-4-methyl-5-methoxy-2,4-dihydro-3H-1,2,4-triazol-3-one, methyl 4-iodo-2-[[[[(4-methoxy-6-methyl-1,3,5-triazin-2-yl)amino]carbonyl]amino]sulfonyl]benzoate, and methyl 2-[4,6-dimethoxypyrimidin-2-ylcarbamoyl)sulfamoyl]-6-(trifluoromethyl)nicotinate, monosodium salt are also known to posses a herbicidal activity.

SUMMARY OF THE INVENTION

The instant invention provides herbicidal compositions possessing a broad herbicidal spectrum. In this regard, the herbicidal compositions of the instant invention can control weeds which typically outbreak in cultivated or non-cultivated fields, and more particularly weeds which are usually problematic in wheat, barley, rye, and oats fields, or the like.

The instant invention further provides herbicidal compositions possessing an excellent herbicidal activity. As such, the herbicidal compositions of the instant invention can be herbicidally active at a low dosage thereof. The herbicidal compositions of the instant invention can also be herbicidally active by providing a synergistic herbicidal activity which is unexpectedly superior to that exhibited from separately utilizing a 2-chloro-4-fluoro-5-(4-methyl-5-trifluoromethyl-3-pyridazinon-2-yl)phenyl $C_{1-5}$ non-cyclic hydrocarbyl ether compound, 1-(2-ethylsulfonylimidazo[1,2-a]pyridin-3-ylsulfonyl)-3-(4,6-dimethoxypyrimidin-2-yl) urea, 2-(2-trifluoromethoxy-phenyl-sulfonylaminocarbonyl)-4-methyl-5-methoxy-2,4-dihydro-3H-1,2,4-triazol-3-one, methyl 4-iodo-2-[[[[(4-methoxy-6-methyl-1,3,5-triazin-2-yl)amino]carbonyl]amino]sulfonyl]benzoate, or methyl 2-[4,6-dimethoxypyrimidin-2-ylcarbamoyl)sulfamoyl]-6-(trifluoromethyl)nicotinate, monosodium salt as an active herbicidal ingredient of a composition.

Furthermore, the instant invention provides methods of controlling a weed or weeds which typically outbreak in cultivated or non-cultivated fields. Preferably, such methods of the instant invention use the inventive herbicidal compositions on the weed(s) or on the soil of said fields.

In order to fulfill such properties, the instant invention provides a herbicidal composition typically comprising a 2-chloro-4-fluoro-5-(4-methyl-5-trifluoromethyl-3-pyridazinon-2-yl)phenyl $C_{1-5}$ non-cyclic hydrocarbyl ether compound and at least another herbicidally active compound selected from a group consisting of 1-(2-ethylsulfonylimidazo[1,2-a]pyridin-3-ylsulfonyl)-3-(4,6-dimethoxypyrimidin-2-yl) urea, 2-(2-trifluoromethoxy-phenyl-sulfonylaminocarbonyl)-4-methyl-5-methoxy-2,4-dihydro-3H-1,2,4triazol-3-one, methyl 4-iodo-2-[[[[(4-methoxy-6-methyl-1,3,5-triazin-2-yl)amino]carbonyl]amino]sulfonyl]benzoate, and methyl 2-[4,6-dimethoxypyridin-2-ylcarbamoyl)sulfamoyl]-6-(trifluoromethyl)nicotinate, monosodium salt, as well as methods of utilizing said compounds.

DETAILED DESCRIPTION OF THE INVENTION

Hereinafter, 1-(2-ethylsulfonylimidazo[1,2-a]pyridin-3-ylsulfonyl)-3-(4,6-dimethoxypyrimidin-2-yl) urea is referred to as its common name of "sulfosulfuron", 2-(2-trifluoromethoxy-phenyl-sulfonylaminocarbonyl)-4-methyl-5-methoxy-2,4-dihydro-3H-1,2,4triazol-3-one is referred to as its common name of "flucarbazone", methyl 4-iodo-2-[[[[(4-methoxy-6-methyl-1,3,5-triazin-2-yl)amino]carbonyl]amino]sulfonyl]benzoate is referred to as its common name of "iodosulfuron", and methyl 2-[4,6-dimethoxypyrimidin-2-ylcarbamoyl)sulfamoyl]-6-(trifluoromethyl)nicotinate, monosodium salt is referred to as its common name of "flupyrsulfuron". Sulfosulfuron is a compound disclosed on page 57 of *Brighton Crop Protection Conference-Weeds*-1995. Flucarbazone is a compound disclosed in U.S. Pat. No. 5,541,337. Iodosulfuron is a compound disclosed on page 22 of *AGROW*, No.297, 1998 publication (PJB publications Ltd). Flupyrsulfuron is a compound disclosed on page 49 of *Brighton Crop Protection Conference-Weeds*-1995.

A herbicidal composition of the instant invention comprises the 2-chloro4-fluoro-5-(4-methyl-5-trifluoromethyl-3-pyridazinon-2-yl)phenyl $C_{1-5}$ non-cyclic hydrocarbyl ether compound and at least one selected from a group consisting of sulfosulfuron, flucarbazone, iodosulfuron and flupyrsulfuron. A weight to weight ratio of the 2-chloro-4-fluoro-5-(4-methyl-5-trifluoromethyl-3-pyridazinon-2-yl) phenyl $C_{1-5}$ non-cyclic hydrocarbyl ether compound to sulfosulfuron, flucarbazone, iodosulfuron, flupyrsulfuron or combinations thereof, in the herbicidal compositions of the instant invention, typically depends on the type of objective weed to be controlled by using said herbicidal compositions, and the situation and condition of utilizing said herbicidal compositions. Even if so, it is preferable in the herbicidal compositions of the instant invention to have the weight to weight ratio of the 2-chloro-4-fluoro-5-(4-methyl-5-trifluoromethyl-3-pyridazinon-2-yl)phenyl $C_{1-5}$ non-cyclic hydrocarbyl ether compound to sulfosulfuron, flucarbazone, iodosulfuron, flupyrsulfuron or combinations thereof at about from 1:0.05 to 1:500.

2-chloro4-fluoro-5-(4-methyl-5-trifluoromethyl-3-pyridazinon-2-yl)phenyl $C_{1-5}$ non-cyclic hydrocarbyl ether compounds which are utilized in the inventive herbicidal compositions are encompassed by the following formula (1):

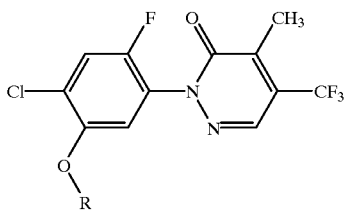

(I)

wherein R represents a $C_{1-5}$ non-cyclic hydrocarbyl group. Preferably, said 2-chloro-4-fluoro-5-(4-methyl-5-trifluoromethyl-3-pyridazinon-2-yl)phenyl $C_{1-5}$ non-cyclic hydrocarbyl ether compounds have R in formula (1) represent a $C_{1-5}$ alkyl, $C_{2-5}$ alkenyl, $C_{2-5}$ alkynyl group, or the like, and most preferably, a group provided in the following Table 1.

TABLE 1

| R | Compound Code* |
|---|---|
| 2-propynyl | A |
| 1-methyl-2-propynyl | B |
| allyl | C |
| 1-methylallyl | D |
| ethyl | E |
| isopropyl | F |

*The compound code provides letter codes which are used herein to designate a 2-chloro-4-fluoro-5-(4-methyl-5-trifluoromethyl-3-pyridazinon-2-yl) phenyl $C_{1-5}$ non-cyclic hydrocarbyl ether compound which comprises the corresponding R group.

2-chloro-4-fluoro-5-(4methyl-5-trifluoromethyl-3-pyridazinon-2-yl)phenyl $C_{1-5}$ non-cyclic hydrocarbyl ether compounds which are utilized in the instant invention may be produced according to the disclosure of WO 97/07104.

The herbicidal compositions of the instant invention are typically formulated as emulsifiable concentrates, wettable powders, suspensible concentrates, granules, or the like by adding solid or liquid carrier(s), surfactant(s), other formulation auxiliaries, or the like, but are not limited thereto. The formulations of the inventive herbicidal compositions typically comprise the 2-chloro-4-fluoro-5-(4-methyl-5-trifluoromethyl-3-pyridazinon-2-yl)phenyl $C_{1-5}$ non-cyclic hydrocarbyl ether compound in combination with said at least one selected from a group consisting of sulfosulfuron, flucarbazone, iodosulfuron and flupyrsulfuron, in a combined amount of from about 0.5 to 90% by weight, and preferably about 1 to 80% by weight, wherein said weight percentages are based on the total weight of the provided herbicidal composition. The formulations of the inventive compositions can be formulated by mixing each formulation of the above components. For example, a herbicidal composition of the instant invention may be produced by formulating the 2-chloro-4-fluoro-5-(4-methyl-5-trifluoromethyl-3 -pyridazinon-2-yl)phenyl $C_{1-5}$ non-cyclic hydrocarbyl ether compound into a suitable formulation, formulating sulfosulfuron, flucarbazone, iodosulfuron, flupyrsulfluron, or combinations thereof into a second suitable formulation, and mixing said 2-chloro-4-fluoro-5-(4-methyl-5-trifluoromethyl-3-pyridazinon-2-yl)phenyl $C_{1-5}$ non-cyclic hydrocarbyl ether compound formulation and said second formulation together.

Examples of solid carriers which can be utilized in the herbicidal compositions of the instant invention usually include small granules or powders. Preferably, such small granules or powders which are utilized in the herbicidal compositions of the instant invention include clays such as kaolinite, diatomaceous earth, synthetic hydrated silicon oxide, Fubasami clay, bentonite and acid clay, talc, other inorganic minerals such as sericite, powdered quartz, powdered sulfur, activated carbon and calcium carbonate, chemical fertilizers such as ammonium sulfate, ammonium phosphate, ammonium nitrate, ammonium chloride and urea, or the like.

Examples of liquid carriers which can be utilized in the herbicidal compositions of the instant invention usually include water, alcohols such as methanol and ethanol, ketones such as acetone, methyl ethyl ketone and cyclohexanone, aromatic hydrocarbons such as toluene, xylene, ethylbenzene and methylnaphthalene, non-aromatic hydrocarbons such as hexane, cyclohexane and kerosine, esters such as ethyl acetate and butyl acetate, nitrites such as acetonitrile and isobutylonitrile, ethers such as dioxane and diisopropyl ether, acid amides such as dimethylformamide and dimethylacetamide, halogenated hydrocarbons such as dichloroethane and trichloroethylene, and the like, but are not limited thereto.

Examples of surfactants which may be utilized in the herbicidal compositions of the instant invention usually include alkylsulfate esters, alkylsulfonate salts, alkylarylsulfonate salts, alkyl aryl ethers and polyoxyethylene derivatives thereof, polyethylene glycol ethers, polyhydric alcohol esters, sugar alcohol derivatives, and the like, but are not limited thereto.

Examples of the other formulation auxiliaries which may be utilized in the herbicidal compositions of the instant invention usually include adhesive and/or dispersing agents, stabilizers, and the like, but are not limited thereto. More specific examples of said adhesive and/or dispersing agents usually include casein, gelatin, lignin derivatives, bentonite, polysaccharides such as powdered starch, gum arabic, cellulose derivatives and alginic acid, synthetic water-soluble polymers such as polyvinyl alcohol, polyvinyl pyrrolidone and polyacrylic acid, and the like. More specific examples of the stabilizers usually include PAP (isopropyl acid phosphate), BHT (2,6-di-tert-butyl4-methylphenol), BHA (2-tert-butyl-4-methyoxyphenol and/or 3-tert-butyl-4-methyoxyphenol), vegetable oils, mineral oils, fatty acids, fatty acid esters, and the like.

If so desired, the herbicidal compositions of the instant invention may further comprise other well known herbicides, so that the herbicidal activity thereof is enhanced. Further, the herbicidal compositions of the instant invention may also optionally comprise insecticides, acaricides, bacteriocides, fungicides, plant growth regulators, fertilizers, safeners, soil conditioners, and the like, if additional functions are desirous therefor.

A herbicidal method of the instant invention typically comprises utilizing or applying a 2-chloro-4-fluoro-5-(4-methyl-5-trifluoromethyl-3-pyridazinon-2-yl) phenyl $C_{1-5}$ non-cyclic hydrocarbyl ether compound and at least one selected from a group consisting of sulfosulfuron, flucarbazone, iodosulfuron and flupyrsulfuron, on the objective weed(s) or on soil which is in a locus of where a control of a weed or weeds is desirous. Preferably, the methods of the instant invention utilize such compounds by applying the inventive herbicidal compositions to such locations.

The herbicidal effect resulting from utilizing or applying a 2-chloro-4-fluoro-5-(4-methyl-5-trifluoromethyl-3-pyridazinon-2-yl)phenyl $C_{1-5}$ non-cyclic hydrocarbyl ether compound in combination with at least one selected from a group consisting of sulfosulfuron, flucarbazone, iodosulfuron and flupyrsulfuron in the methods of the instant invention typically depends on the amount of the utilized inventive composition, the time of utilization, weather condition(s), formulation form(s), location(s) of utilization, objective weed(s) or the like, or combinations thereof Further, when such compounds are utilized to benefit crops, the combined amount of said compounds utilized in the inventive methods may also depend on the type of objective crop that benefits from the utilization thereof. Even if so, the 2-chloro-4-fluoro-5-(4-methyl-5-trifluoromethyl-3-pyridazinon-2-yl) phenyl $C_{1-5}$ non-cyclic hydrocarbyl ether compound and at least one selected from the group consisting of sulfosulfuron, flucarbazone, iodosulfuron and flupyrsulfuron, are preferably utilized in the inventive methods at a dosage of from about 0.1 to 500 g per 1 ha.

Such utilization or application of the inventive herbicidal compositions in the methods of the instant invention can be in various types of locations. Since the herbicidal compositions of the instant invention possess a herbicidal activity against various types of weeds, the methods of the instant invention can utilize the inventive herbicidal compositions in non-cultivated fields. Examples of said non-cultivated fields include training facilities, open fields, woodlands, boundaries of railroad tracks, and the like. Further, since the inventive herbicidal compositions additionally possess a selectivity which selectively controls weeds without causing problematic phytotoxicity to crops, the methods of the instant invention can also utilize the inventive herbicidal compositions in cultivated fields. Examples of said cultivated fields include the standard cultivated field, a cultivated field which is non-tillaged, horticultural fields such as orchards, and the like. However, such cases in which the methods of the instant invention utilize the inventive herbicidal compositions in cultivated fields, should not cause problematic phytotoxicity to crops, when crops are present, and especially to crops such as barleys, wheats, ryes, oats or the like.

It should be noted that the methods of the instant invention are not limited to such locations, since it is well known that weeds may emerge in additional locations in which the inventive herbicidal compositions would be applicable.

Examples of the weeds controllable with the herbicidal methods of the instant invention include Dicotyledoneae plants such as common chickweed (*Stellaria media*), Cleavers (*Galium aparine*), Persian speedwell (*Veronica persica*), Ivyleaf speedwell (*Veronica hederifolia*), Field pansy (*Viola arvensis*), Wild pansy (*Viola tricolor*), Purple deadnettle (*Lamium purpureum*), Henbit (*Lamium amplexicaure*), Shepherdspurse (*Capsella bursa-pastoris*), Annual sowthistle (*Sonchus oleraceus*), Corn poppy (*Papaver rhoeas*), Scentless chamomile (*Matricaria inodora*), Wild chamomile (*Matricaria chamomilla*), Wild mustard (*Sinapsis arvensis*), Field forget-me-not (*Myosotis arvensis*), Wild buckwheat (*Polygonm convolvulus*), Common lambsquarters (*Chenopodium album*), Kochia (*Kochia scoparia*), Smooth pigweed (*Amaranthus hybridus*) and Redroot pigweed (*Amaranthus retrofexus*), Monocotyledoneae such as Barnyardgrass (*Echinochloa crus-galli*), Green foxtail (*Setaria viridis*), Giant foxtail (*Setaria faveri*), Annual bluegrass (*Poa annua*), Blackgrass (*Alopecurus myosuroides*), Italian ryegrass (*Lolium multiflorum*), Downy brome (*Bromus tectorum*) and Wild oat (*Avena fatua*), and the like.

The methods of the instant invention may optionally utilize or apply a formulated inventive herbicidal composition on said weed or soil by diluting the provided formulation of the inventive herbicidal composition, preferably with water. For example, the methods of the instant invention may dilute emulsifiable concentrates, wettable powders, or suspensible concentrates of the inventive herbicidal compositions by diluting such formulations with 100 to 1000 liters of water per 1 ha of a locus in which a control of a weed or weeds is desirous.

EXAMPLES

Hereinafter, the instant invention is further described by providing the following examples, but it is to be understood that the instant invention is not to be limited by the following examples.

Formulation Example 1

Ten (10) parts by weight of Compound A, Compound B, Compound C, Compound D, Compound E or Compound F, 15 parts by weight of sulfosulfuron, flucarbazone, iodosulfuron or flupyrsulfuron, 3 parts by weight of calcium ligninsulfonate, 2 parts by weight of sodium laurylsulfate and 70 parts by weight of synthetic hydrated silicon oxide are well pulverized and mixed to achieve a wettable powder formulation of the instant invention.

Formulation Example 2

Ten (10) parts by weight of Compound A, Compound B, Compound C, Compound D, Compound E, or Compound F, 15 parts by weight of sulfosulfuron, flucarbazone, iodosulfuron or flupyrsulfuron, 3 parts by weight of polyoxyethylene sorbitan monolaurate, 3 parts by weight of CMC (carboxymethyl cellulose) and 69 parts by weight of water are mixed, and pulverized until the particle diameter thereof is 5 microns or less to achieve a suspensible concentrate formulation of the instant invention.

Formulation Example 3

Four (4) parts by weight of Compound A, Compound B, Compound C, Compound D, Compound E, or Compound F, 6 parts by weight of sulfosulfuron, flucarbazone, iodosulfuron or flupyrsulfuron, 14 parts by weight of polyoxyethylenestyryl phenyl ether, 6 parts by weight of calcium dodecylbenzenesulfonate, 35 parts by weight of xylene, and 35 parts by weight of cyclohexane are well mixed to achieve an emulsifiable concentrate formulation of the instant invention.

Formulation Example 4

Two (2) parts by weight of Compound A, Compound B, Compound C, Compound D, Compound E, or Compound F, and 3 parts by weight of sulfosulfuron, flucarbazone, iodosulfuron or flupyrsulfuron are added to 40 parts by weight of an aqueous solution of 10% polyvinyl alcohol, and then emulsification dispersed by using a homogenizer until the average particle diameter thereof is 10 $\mu$m or less. Subsequently, 55 parts by weight of water is added thereto, to achieve a concentrated emulsion formulation of the instant invention.

Formulation Example 5

A mixture is formed by pulverizing and ten mixing 1 part by weight of Compound A, Compound B, Compound C, Compound D, Compound E, or Compound F, 1 part by weight of sulfosulfuron, flucarbazone, iodosulfuron or flupyrsulfuron, 2 parts by weight of synthetic hydrated silicon oxide, 2 parts by weight of calcium lignin sulfonate, 30 parts by weight of bentonite and 64 parts by weight of kaolin clay, to achieve a mixture. After water is added to the mixture, the mixture is kneaded and granulation dried to achieve a granule formulation of the instant invention.

Formulation Example 6

Ten (10) parts by weight of Compound A, Compound B, Compound C, Compound D, Compound E or Compound F, 15 parts by weight of a mixture comprising sulfosulfuron and flucarbazone at weight to weight basis of 1:1, 3 parts by weight of calcium ligninsulfonate, 2 parts weight of sodium laurylsulfate and 70 parts by weight of synthetic hydrated silicon oxide are well pulverized and mixed to achieve a wettable powder formulation of the instant invention.

Formulation Example 7

Ten (10) parts by weight of Compound A, Compound B, Compound C, Compound D, Compound E or Compound F, 15 parts by weight of a mixture comprising iodosulfuron and flupyrsulfuron at a weight to weight basis of 1:1, 3 parts by weight of calcium ligninsulfonate, 2 parts by weight of sodium laurylsulfate and 70 parts by weight of synthetic hydrated silicon oxide are well pulverized and mixed to achieve a wettable powder formulation of the instant invention.

Standards of Scores

The herbicidal activity of a herbicidal composition and the phytotoxicity caused by the herbicidal composition were evaluated in the following test examples at 11 levels, using the indices of 0 to 10, i.e., shown by "0", "1", "2", "3", "4", "5", "6", "7", "8", "9", or "10". Said indices provide numerical scores that ascend with the level of herbicidal activity or phytotoxicity. In scoring the herbicidal activity of a provided herbicidal composition, a score of "10" means that the test plants (crops and/or weeds) died completely or their germination or growth were completely inhibited and a score of "0" means that there was no or little difference in the degree of germination or growth between treated plants to untreated plants at the time of examination. Similarly, in scoring the phytotoxicity of a provided herbicidal composition, a low score means that the phytotoxicity is at a level which is practically not a problem, and a high score means that the phytotoxicity is at an unacceptable level.

Test Example 1

Plastic pots in which the bottom surface thereof had an area of 246 cm$^2$ and which had a depth of 14 cm, were filled with upland soil and seeded with wheat, Scentless chamomile (*Matricaria inodora*), and Field pansy (*Viola arvensis*), respectively. The plastic pots containing wheat were given 13 days to grow in a greenhouse. The plastic pots containing Scentless chamomile and plastic pots containing Field pansy were given 20 days to grow in a greenhouse.

A suspensible concentrate of Compound A was formulated by forming a mixture comprising 5 parts by weight of Compound A, 2 parts by weight of alkylaryl ether, 1 part by weight of xanthan gum, 10 parts by weight of propylene glycol, 1 part by weight of a silicon-type emulsion, and 81 parts by weight of water, and then wet pulverizing the achieved mixture until the particle diameter thereof was 2 microns or less.

The suspensible concentrate of Compound A, a sulfosulfuron formulation product (Commercial name: Monitor, commercially available by MONSANTO COMPANY), and a mixture containing the suspensible concentrate of Compound A and the sulfosulfuron formulation product were diluted with water. The resulting diluted compositions are shown in Table 2. Each of the diluted compositions was then uniformly sprayed, respectively, over the wheat, Scentless chamomile, and Field pansy by using a small sprayer. After such applications of said compositions, the wheat, the Scentless chamomile, and the Field pansy were grown in a greenhouse for 18 days. The herbicidal activity of said compositions (which relates to the Scentless chamomile and Field pansy), as well as the phytotoxicity of said compositions (which relates to the wheat), were then examined in accordance to the above standards of scores. The results are shown in Table 2.

TABLE 2

| Tested Compositions | Dosage (g/1 ha) | Phytotoxicity wheat | Herbicidal activity | |
|---|---|---|---|---|
| | | | Scentless Chamomile | Field pansy |
| Compound A | 1.25 | 0 | 3 | 5 |
| Sulfosulfuron | 5 | 0 | 2 | 1 |
| Compound A + Sulfosulfuron | 1.25 + 5 | 0 | 7 | 8 |

Test Example 2

Plastic pots in which the bottom surface thereof had an area of 246 cm$^2$ and which had a depth of 12.5 cm, were filled with upland soil and seeded with wheat, Barnyardgrass (*Echinochloa crus-galli*), and Wild oat (*Avena fatua*). The plastic pots containing wheat, Barnyardgrass and Wild oat were given 16 days to grow in a greenhouse.

An emulsifiable concentrate of flucarbazone was formulated by mixing 10 parts by weight of flucarbazone, with 3 parts by weight of polyoxyethylene styryl phenyl ether, 2 parts by weight of calcium dodecylbenzenesulfonate and 85 parts by weight of xylene.

A suspensible concentrate of Compound A was formulated by mixing S parts by weight of Compound A, with 2 parts by weight of alkylaryl ether, 1 part by weight of xanthan gum, 10 parts by weight of propylene glycol, I part by weight of a silicon-type emulsion and 81 parts by weight of water, and then wet pulverizing the achieved mixture until the particle diameter thereof was 2 microns or less.

The emulsifiable concentrate of flucarbazone, the suspensible concentrate of Compound A, a mixture containing the emulsifiable concentrate of flucarbazone and the suspensible concentrate of Compound A were diluted with water. The resulting diluted compositions are shown in Table 3. Each of the diluted compositions was then uniformly sprayed onto the wheat, Barnyardgrass, and Wild oat by using a small sprayer. After the plastic pots containing the wheat, Barnyardgrass, and Wild oat were sprayed with one of the provided compositions, said plastic pots were placed in a greenhouse for 7 days. The herbicidal activity of said compositions (which relates to the Barnyardgrass and Wild oat), as well as the phytotoxicity of said compositions (which relates to the wheat), were then examined in accordance to the above standards of scores. The results are shown in Table 3.

TABLE 3

| Tested Compositions | Dosage (g/1 ha) | Phytotoxicity wheat | Herbicidal activity | |
|---|---|---|---|---|
| | | | Barnyardgrass | Wild oat |
| Compound A | 2 | 0 | 6 | 1 |
| flucarbazone | 30 | 0 | 0 | 2 |
| Compound A + flucarbazone | 2 + 30 | 0 | 9 | 7 |

The above scores that result from Test example 1 and 2 evidence that the herbicidal compositions of the instant invention provide a superior and synergistic herbicidal activity, as well as a safety, which relates to crops, by averting problematic phytotoxicity thereto. Such test results also evidence that by simply using one of the active ingredients of the inventive herbicidal compositions, without the other active ingredient of the inventive herbicidal compositions, does not result in such superior and synergistic herbicidal activity.

Each of the patent documents and publications that are mentioned in the instant specification are incorporated herein by reference in their entirety.

What is claimed is:

1. A herbicidal composition comprising as active ingredient therein:
   (i) a 2-chloro-4-fluoro-5-(4-methyl-5-trifluoromethyl-3-pyridazinon-2-yl)phenyl $C_{1-5}$ non-cyclic hydrocarbyl ether compound, and
   (ii) at least one compound selected from a group consisting of 1-(2-ethylsulfonylimidazo[1,2-a]pyridin-3-ylsulfonyl)-3-(4,6-dimethoxypyrimidin-2-yl urea, 2-(2-trifluoromethoxy-phenyl-sulfonylaminocarbonyl)-4-methyl-5-methoxy-2,4-dihydro-3H-1,2,4-triazol-3-one, methyl 4-iodo-2-[[[[(4-methoxy-6-methyl-1,3,5-triazin-2-yl)amino]carbonyl]amino]sulfonyl]benzoate, and methyl 2-[4,6-dimethoxypyrimidin-2-ylcarbamoyl)sulfamoyl]-6-(trifluoromethyl)nicotinate, monosodium salt.

2. The herbicidal composition according to claim 1, wherein said composition comprises:
   (i) the 2-chloro-4-fluoro-5-(4-methyl-5-trifluoromethyl-3-pyridazinon-2-yl) phenyl $C_{1-5}$ non-cyclic hydrocarbyl ether compound, and
   (ii) the 1-(2-ethylsulfonylimidazo[1,2-a]pyridin-3-ylsulfonyl)-3-(4,6-dimethoxypyrimidin-2-yl) urea.

3. The herbicidal composition according to claim 1, wherein said composition comprises:
   (i) the 2-chloro-4-fluoro-5-(4-methyl-5-trifluoromethyl-3-pyridazinon-2-yl) phenyl $C_{1-5}$ non-cyclic hydrocarbyl ether compound, and
   (ii) the 2-(2-trifluoromethoxy-phenyl-sulfonylaminocarbonyl)-4-methyl-5-methoxy-2,4-dihydro-3H-1,2,4-triazol-3-one.

4. The herbicidal composition according to claim 1, wherein said composition comprises:
   (i) the 2-chloro-4-fluoro-5-(4-methyl-5-trifluoromethyl-3-pyridazinon-2-yl) phenyl $C_{1-5}$ non-cyclic hydrocarbyl ether compound, and
   (ii) the methyl 4-iodo-2-[[[[(4-methoxy-6-methyl-1,3,5-triazin-2-yl)amino]carbonyl]amino]sulfonyl]benzoate.

5. The herbicidal composition according to claim 1, wherein said composition comprises:
   (i) the 2-chloro-4-fluoro-5-(4-methyl-5-trifluoromethyl-3-pyridazinon-2-yl) phenyl $C_{1-5}$ non-cyclic hydrocarbyl ether compound, and
   (ii) the methyl 2-[4,6-dimethoxypyrimidin-2-ylcarbamoyl)sulfamoyl]-6-(trifluoromethyl)nicotinate, monosodium salt.

6. The herbicidal composition according to claim 1, wherein a weight to weight ratio of the (i) 2-chloro-4-fluoro-5-(4-methyl-5-trifluoromethyl-3-pyridazinon-2-yl)phenyl $C_{1-5}$ non-cyclic hydrocarbyl ether compound to said (ii) at least one compound selected from a group consisting of 1-(2-ethylsulfonylimidazo[1,2-a]pyridin-3- ylsulfonyl)-3-(4,6-dimethoxypyrimidin-2-yl urea, 2-(2-trifluoromethoxy-phenyl-sulfonylaminocarbonyl)-4-methyl-5-methoxy-2,4-dihydro-3H-1,2,4-triazol-3-one, methyl 4-iodo-2-[[[[(4-methoxy-6-methyl-1,3,5-triazin-2-yl)amino]carbonyl]amino]sulfonyl]benzoate, or methyl 2-[4,6-dimethoxypyrimidin-2-ylcarbamoyl)sulfamoyl]-6-(trifluoromethyl)nicotinate, monosodium salt, is about from 1:0.05 to 1:500.

7. The herbicidal composition according to claim 6, wherein the composition additionally comprises a solid carrier or a liquid carrier.

8. The herbicidal composition according to claim 1, wherein the 2-chloro-4-fluoro-5-(4-methyl-5-trifluoromethyl-3-pyridazinon-2-yl)phenyl $C_{1-5}$ non-cyclic hydrocarbyl ether is a compound of formula (I):

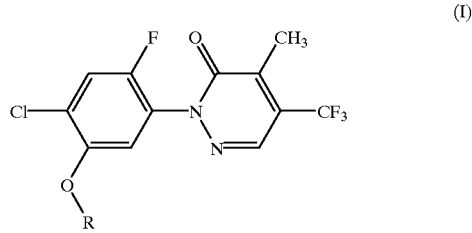

(I)

wherein R represents a $C_{1-5}$ non-cyclic hydrocarbyl group.

9. The herbicidal composition according to claim 8, wherein said R represents a 2-propynyl, 1-methyl-2-propynyl, allyl, 1-methylallyl, ethyl, or isopropyl group in formula (I).

10. A method of controlling a weed, which comprises applying an effective amount of:
    (i) a 2-chloro-4-fluoro-5-(4-methyl-5-trifluoromethyl-3-pyridazinon-2-yl)phenyl $C_{1-5}$ non-cyclic hydrocarbyl ether compound, and
    (ii) at least one compound selected from a group consisting of 1-(2-ethylsulfonylimidazo[1,2-a]pyridin-3-ylsulfonyl)-3-(4,6-dimethoxypyrimidin-2-yl urea, 2-(2-trifluoromethoxy-phenyl-sulfonylaminocarbonyl)-4-methyl-5-methoxy-2,4-dihydro-3H-1,2,4-triazol-3-one, methyl 4-iodo-2-[[[[(4-methoxy-6-methyl-1,3,5-triazin-2-yl)amino]carbonyl]amino]sulfonyl]benzoate, and methyl 2-[4,6-dimethoxypyrimidin-2-ylcarbamoyl)sulfamoyl]-6-(trifluoromethyl)nicotinate, monosodium salt,
   to a non-cultivated field or a cultivated field.

11. A method of controlling weeds, which comprises applying an effective amount of:
    (i) a 2-chloro-4-fluoro-5-(4-methyl-5-trifluoromethyl-3-pyridazinon-2-yl)phenyl $C_{1-5}$ non-cyclic hydrocarbyl ether compound, and
    (ii) at least one compound selected from a group consisting of 1-(2-ethylsulfonylimidazo[1,2-a]pyridin-3-ylsulfonyl)-3-(4,6-dimethoxypyrimidin-2- yl urea, 2-(2-trifluoromethoxy-phenyl-sulfonylaminocarbonyl)- 4-methyl-5-methoxy-2,4-dihydro-3H-1,2,4-triazol-3-one, methyl 4-iodo-2-[[[[(4-methoxy-6-methyl-1,3,5-triazin-2-yl)amino]carbonyl]amino]sulfonyl]benzoate, and methyl 2-[4,6-dimethoxypyrimidin-2-ylcarbamoyl)sulfamoyl]-6-(trifluoromethyl)nicotinate, monosodium salt, to the weed or soil.

12. The method according to claim 11, wherein the weed is in a wheat, barley, rye, or oats field.

13. The method according to claim 10 or 11, wherein the effective amount is 0.1 to 500 g per 1 ha.

14. The method according to claim 13, wherein a weight ratio of the (i) a 2-chloro-4-fluoro-5-(4-methyl-5-trifluoromethyl-3-pyridazinon-2-yl)phenyl $C_{1-5}$ non-cyclic hydrocarbyl ether compound, and
    (ii) at least one compound selected from a group consisting of 1-(2-ethylsulfonylimidazo[1,2-a]pyridin-3- ylsulfonyl)-3-(4,6-dimethoxypyrimidin-2-yl urea, 2-(2-trifluoromethoxy-phenyl-sulfonylaminocarbonyl)-4-methyl-5-methoxy-2,4-dihydro-3H-1,2,4-triazol-3-one, methyl 4-iodo-2-[[[[(4-methoxy-6-methyl-1,3,5-triazin-2-yl)amino]carbonyl]amino]sulfonyl]benzoate, and methyl 2-[4,6-dimethoxypyrimidin-2-ylcarbamoyl)sulfamoyl]-6-(trifluoromethyl)nicotinate, monosodium salt, is at about 0:0.05 to 1:500.

* * * * *